(12) United States Patent
Bender et al.

(10) Patent No.: US 10,827,919 B2
(45) Date of Patent: Nov. 10, 2020

(54) RECONFIGURABLE OPTICAL COHERENCE TOMOGRAPHY (OCT) SYSTEM

(71) Applicant: Alcon Inc., Fribourg (CH)

(72) Inventors: Craig Bender, Laguna Niguel, CA (US); Michael Papac, North Tustin, CA (US); Lingfeng Yu, Rancho Santa Margarita, CA (US)

(73) Assignee: Alcon Inc., Fribourg (CH)

( * ) Notice: Subject to any disclaimer, the term of this patent is extended or adjusted under 35 U.S.C. 154(b) by 20 days.

(21) Appl. No.: 15/958,904

(22) Filed: Apr. 20, 2018

(65) Prior Publication Data

US 2018/0317764 A1 Nov. 8, 2018

Related U.S. Application Data

(60) Provisional application No. 62/500,339, filed on May 2, 2017.

(51) Int. Cl.
*A61B 3/00* (2006.01)
*A61B 3/14* (2006.01)
(Continued)

(52) U.S. Cl.
CPC .............. *A61B 3/102* (2013.01); *A61B 3/13* (2013.01); *A61B 5/0066* (2013.01); *A61F 9/008* (2013.01);
(Continued)

(58) Field of Classification Search
CPC ..... A61B 5/0066; A61B 3/102; A61B 5/6852; A61B 5/0084; A61B 5/0073;
(Continued)

(56) References Cited

U.S. PATENT DOCUMENTS 5,493,109 A 2/1996 Wei et al.
5,795,295 A 8/1998 Hellmuth et al.
(Continued)

FOREIGN PATENT DOCUMENTS

CN 1924633 A 3/2007
CN 200953060 U 9/2007
(Continued)

OTHER PUBLICATIONS

EnFocus Intrasurgical OCT [brochure]. Switzerland: Leica Microsystems GmbH, 2017.
(Continued)

*Primary Examiner* — Brandi N Thomas

(57) ABSTRACT

An optical coherence tomography (OCT) apparatus includes an optical source module comprising two or more selectable optical sources or an optical source configured to selectively operate in two or more source operating modes, or a combination of both, and further comprises an OCT engine coupled to the optical source module, the OCT engine comprising an OCT interferometer. The OCT apparatus still further includes a mode-switching optics module coupled to the OCT engine and comprising one or more swappable, selectable, or adjustable optical components, such that the mode-switching optics module is configured to selectively provide two or more optical configurations for the optical path between the OCT engine and an imaged object, according to two or more corresponding operating modes.

18 Claims, 6 Drawing Sheets

(51) Int. Cl.
*A61B 3/10* (2006.01)
*A61B 3/13* (2006.01)
*A61B 5/00* (2006.01)
*A61F 9/008* (2006.01)
*G01B 9/02* (2006.01)

(52) U.S. Cl.
CPC ............... *G01B 9/02091* (2013.01); *A61F 2009/00851* (2013.01)

(58) Field of Classification Search
CPC ........ A61B 1/00172; A61B 2090/3735; A61B 2562/0233; A61B 5/0035; A61B 5/0059; A61B 1/00096; A61B 1/313; A61B 3/1005; A61B 3/103; A61B 3/107; A61B 1/0002; A61B 1/00094; A61B 1/00165; A61B 1/00179; A61B 1/00188; A61B 1/018; A61B 2034/108; A61B 2562/043; A61B 2562/063; A61B 3/0025; A61B 3/0041; A61B 5/04001; A61B 8/12; A61B 5/0046; A61B 8/4416; A61B 8/5261; A61B 1/00183; A61B 2560/0437
USPC ............... 351/200, 205–206, 209–211, 221, 351/243–246
See application file for complete search history.

(56) References Cited

U.S. PATENT DOCUMENTS

| | | | |
|---|---|---|---|
| 6,004,314 | A | 12/1999 | Wei et al. |
| 6,419,360 | B1 | 7/2002 | Hauger et al. |
| 6,485,413 | B1 | 11/2002 | Boppart et al. |
| 6,741,359 | B2 | 5/2004 | Wei et al. |
| 6,741,948 | B2 | 5/2004 | Hauger et al. |
| 6,763,259 | B1 | 7/2004 | Hauger et al. |
| 7,236,251 | B2 | 6/2007 | Takaoka |
| 7,699,468 | B2 | 4/2010 | Gaida |
| 7,791,794 | B2 | 9/2010 | Reimer et al. |
| 7,839,494 | B2 | 11/2010 | Reimer et al. |
| 7,889,423 | B2 | 2/2011 | Reimer et al. |
| 7,901,080 | B2 | 3/2011 | Hauger et al. |
| 7,978,404 | B2 | 7/2011 | Reimer et al. |
| 8,023,120 | B2 | 9/2011 | Reimer et al. |
| 8,042,944 | B2 | 10/2011 | De Vries et al. |
| 8,049,873 | B2 | 11/2011 | Hauger et al. |
| 8,366,271 | B2 | 2/2013 | Izatt et al. |
| 8,425,037 | B2 | 4/2013 | Uhlhorn et al. |
| 8,459,795 | B2 | 6/2013 | Seesselberg et al. |
| 8,777,412 | B2 | 7/2014 | Buckland et al. |
| 8,882,271 | B2 | 11/2014 | Sander |
| 8,891,164 | B2 | 11/2014 | Kuebler et al. |
| 8,922,882 | B2 | 12/2014 | Hauger et al. |
| 9,050,027 | B2 | 6/2015 | Uhlhorn et al. |
| 9,060,712 | B2 | 6/2015 | Buckland et al. |
| 9,107,618 | B2 | 8/2015 | Huening et al. |
| 9,377,293 | B2 | 6/2016 | Hauger et al. |
| 2011/0026035 | A1 | 2/2011 | Muto et al. |
| 2011/0032479 | A1* | 2/2011 | Utsunomiya ........ A61B 3/0058 351/206 |
| 2011/0261367 | A1 | 10/2011 | Gmitro et al. |
| 2012/0184846 | A1* | 7/2012 | Izatt ................. G02B 21/0012 600/425 |
| 2012/0197102 | A1 | 8/2012 | Hanebuchi et al. |
| 2013/0003018 | A1 | 1/2013 | Utagawa et al. |
| 2013/0083289 | A1 | 4/2013 | Hauger et al. |
| 2014/0024949 | A1 | 1/2014 | Wei et al. |
| 2014/0320626 | A1 | 10/2014 | Kim et al. |
| 2015/0055093 | A1 | 2/2015 | Ehlers et al. |
| 2015/0062531 | A1 | 3/2015 | Buckland |
| 2015/0109580 | A1 | 4/2015 | Hauger et al. |
| 2015/0272697 | A1 | 10/2015 | Shi et al. |
| 2015/0342460 | A1 | 12/2015 | Izatt et al. |
| 2015/0342697 | A1 | 12/2015 | Saur et al. |
| 2016/0007848 | A1 | 1/2016 | Filippatos et al. |
| 2016/0081545 | A1 | 3/2016 | Hauger et al. |
| 2016/0081549 | A1 | 3/2016 | Wilzbach et al. |
| 2016/0089015 | A1 | 3/2016 | Eslami et al. |
| 2016/0095514 | A1 | 4/2016 | Meckes et al. |
| 2016/0192835 | A1 | 7/2016 | Matz et al. |
| 2016/0235299 | A1 | 8/2016 | Yamamoto et al. |

FOREIGN PATENT DOCUMENTS

| | | |
|---|---|---|
| CN | 102710845 A | 10/2012 |
| CN | 203208005 U | 9/2013 |
| CN | 204832040 U | 12/2015 |
| CN | 204839912 U | 12/2015 |
| DE | 102005031496 A1 | 1/2007 |
| DE | 102008059876 A1 | 6/2010 |
| DE | 102009037841 A1 | 2/2011 |
| DE | 102012017833 A1 | 3/2014 |
| DE | 102013210728 A1 | 12/2014 |
| EP | 0697611 A2 | 2/1996 |
| EP | 0815801 A2 | 1/1998 |
| EP | 1225454 A2 | 7/2002 |
| EP | 1508065 A1 | 2/2005 |
| EP | 1918756 A1 | 5/2008 |
| EP | 1933693 A1 | 6/2008 |
| EP | 2124718 A1 | 9/2008 |
| EP | 2103249 A1 | 9/2009 |
| EP | 2453823 A1 | 5/2012 |
| EP | 2688463 A1 | 1/2014 |
| EP | 2786697 A1 | 10/2014 |
| EP | 2833779 A1 | 2/2015 |
| EP | 2949285 A1 | 12/2015 |
| EP | 2965688 A1 | 1/2016 |
| EP | 2997880 A1 | 3/2016 |
| EP | 3005937 A1 | 4/2016 |
| EP | 3010394 A1 | 4/2016 |
| EP | 3035840 A2 | 6/2016 |
| EP | 3039474 A1 | 7/2016 |
| JP | 2008264488 A | 11/2008 |
| JP | 2008264489 A | 11/2008 |
| JP | 2008264490 A | 11/2008 |
| JP | 2013137541 A | 7/2013 |
| KR | 101268413 B1 | 5/2013 |
| KR | 20130101798 A | 9/2013 |
| RU | 2183108 C1 | 6/2002 |
| WO | 2010031540 A2 | 3/2010 |
| WO | 2010031540 A3 | 5/2010 |
| WO | 2010060622 A2 | 6/2010 |
| WO | 2011020606 A2 | 2/2011 |
| WO | 2012100030 A2 | 7/2012 |
| WO | 2013079214 A1 | 6/2013 |
| WO | 2013189591 A1 | 12/2013 |
| WO | 2015041446 A1 | 3/2015 |
| WO | 2015100129 A1 | 7/2015 |
| WO | 2015113917 A1 | 8/2015 |
| WO | 2015166695 A1 | 11/2015 |
| WO | 2015182995 A1 | 12/2015 |
| WO | 2016010725 A1 | 1/2016 |
| WO | 2016055422 A1 | 4/2016 |
| WO | 2016058931 A2 | 4/2016 |
| WO | 2016109015 A1 | 7/2016 |

OTHER PUBLICATIONS

Envisu C2300 OCT [brochure]. Switzerland: Leica Microsystems GmbH, 2017.
Donovan et al. "Microscope-Integrated Optical Coherence Tomography." Retina Today. Jan./Feb. 2016. pp. 52-56.
Ehlers et al. "Visualization of Real-Time Intraoperative Maneuvers with a Microscope-Mounted Spectral Domain Optical Coherence Tomography System." Retina. NIH Public Access. Jan. 2013. vol. 33, No. 1. pp. 232-236.
Hahn et al. A Microscope-IntegratedOCT System for True Intrasurgical OCT Acquisition. Retina Today. Oct. 2012. pp. 61-63.
Ray et al. "Intraoperative Microscope-Mounted Spectral Domain Optical Coherence Tomography for Evaluation of Retinal Anatomy

(56) References Cited

OTHER PUBLICATIONS during Macular Surgery." Ophthalmology. Nov. 2011. vol. 118, No. 11. pp. 2212-2217. Published by Elsevier, Inc.

* cited by examiner

RECONFIGURABLE OPTICAL COHERENCE TOMOGRAPHY (OCT) SYSTEM

TECHNICAL FIELD

Embodiments disclosed herein are related to devices, systems, and methods for adjusting optical performance characteristics in an Optical Coherence Tomography (OCT) system.

BACKGROUND

Current ophthalmic refractive surgical methods, such as cataract surgery, intra-corneal inlays, laser-assisted in situ keratomileusis (LASIK), and photorefractive keratectomy (PRK), rely on ocular biometry data to prescribe the best refractive correction. Historically, ophthalmic surgical procedures used ultrasonic biometry instruments to image portions of the eye. In some cases, these biometric instruments generated a so-called A-scan of the eye: an acoustic echo signal from all interfaces along an imaging axis that was typically aligned with an optical axis of the eye: either parallel with it, or making only a small angle. Other instruments generated a so-called B-scan, essentially assembling a collection of A-scans, taken successively as a head or tip of the biometry instrument was scanned along a scanning line. This scanning line was typically lateral to the optical axis of the eye. These ultrasonic A- or B-scans were then used to measure and determine biometry data, such as an ocular axial Length, an anterior depth of the eye, or the radii of corneal curvature.

In some surgical procedures, a second, separate keratometer was used to measure refractive properties and data of the cornea. The ultrasonic measurements and the refractive data were then combined in a semi-empirical formula to calculate the characteristics of the optimal intra-ocular lens (IOL) to be prescribed and inserted during the subsequent cataract phaco surgery.

More recently, ultrasonic biometry devices have been rapidly giving way to optical imaging and biometry instruments that are built on the principle of Optical Coherence Tomography (OCT). OCT is a technique that enables micron-scale, high-resolution, cross-sectional imaging of the human retina, cornea, or cataract. OCT technology is now commonly used in clinical practice, with such OCT instruments are now used in 80-90% of all IOL prescription cases. Among other reasons, their success is due to the non-contact nature of the imaging and to the higher precision than that of the ultrasound biometers.

Even with these recent advances, however, substantial further growth and development is needed for the functionalities and performance of biometric and imaging instruments.

SUMMARY

An optical coherence tomography (OCT) apparatus according to some embodiments includes an optical source module comprising two or more selectable optical sources or an optical source configured to selectively operate in two or more source operating modes, or a combination of both, and further comprises an OCT engine coupled to the optical source module, the OCT engine comprising an OCT interferometer. The OCT apparatus still further includes a mode-switching optics module coupled to the OCT engine and comprising one or more swappable, selectable, or adjustable optical components, such that the mode-switching optics module is configured to selectively provide two or more optical configurations for the optical path between the OCT engine and an imaged object, according to two or more corresponding operating modes.

A corresponding method, according to some embodiments, is implemented in an optical coherence tomography (OCT) apparatus and comprises controlling an optical source module to select one of two or more selectable optical sources or to select one of two or more source operating modes for an optical source, or a combination of both, and controlling a mode-switching optics module coupled to the optical source module via an OCT engine, the OCT engine comprising an interferometer, to select one or more swappable optical components or to adjust one or more adjustable optical components, so as to select one of two or more selectable optical configurations for the optical path between the OCT engine and an imaged object.

The embodiments described herein may be used to provide and/or operate an all-in-one device to achieve optimized OCT performance for each of several different application modes. Other advantages and variations of the above-summarized embodiments are described below.

DETAILED DESCRIPTION

In the following description, specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

Figure 1:
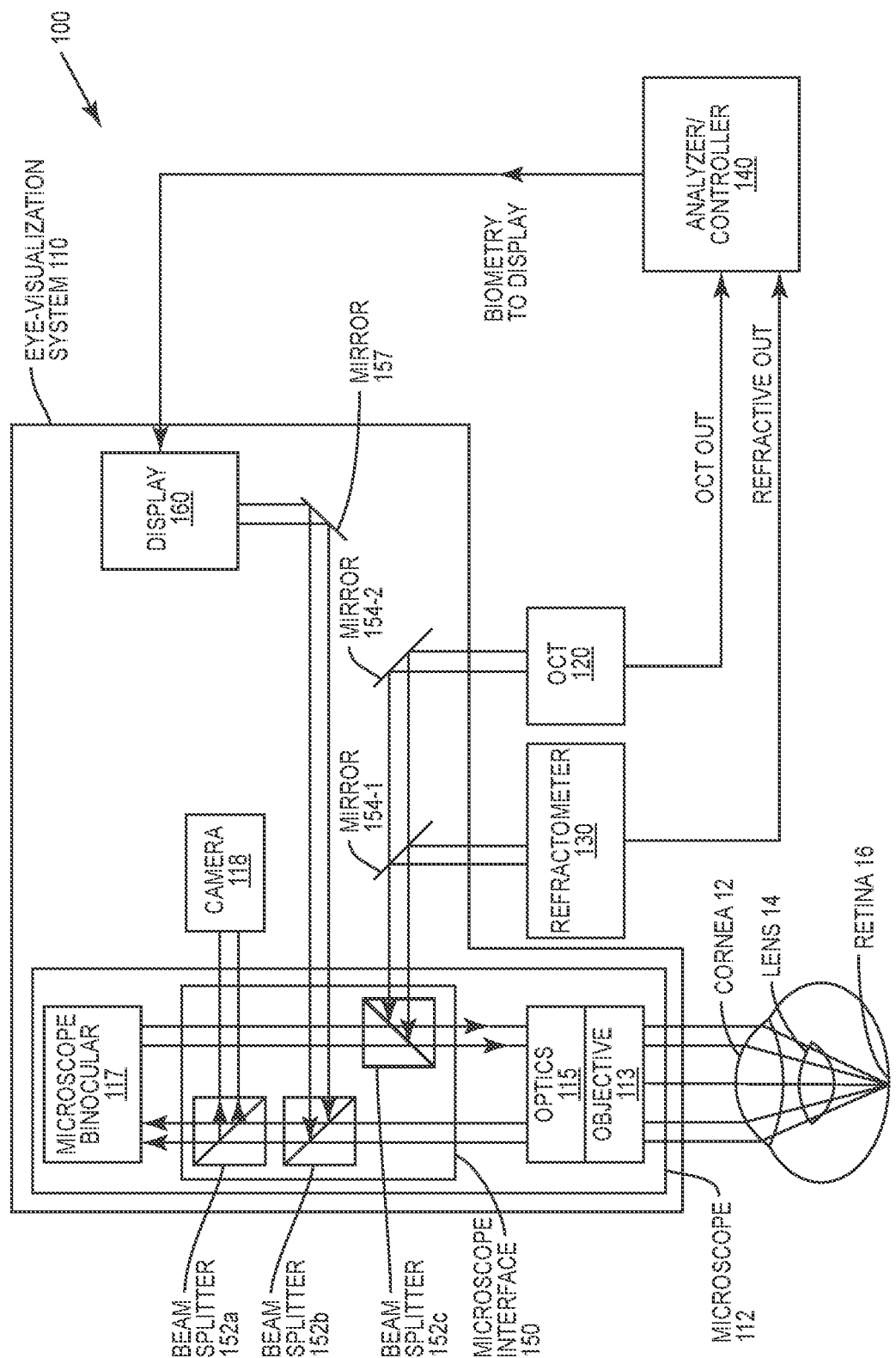
FIG. 1 is a diagram illustrating an Optical Coherence Tomography (OCT) system, consistent with some embodiments.

Embodiments of the presently disclosed techniques and apparatus may be employed in both microscope-mounted and microscope-integrated Optical Coherence Tomography (OCT) systems. FIG. 1 illustrates an example of a microscope-integrated OCT system 100, and is presented to illustrate the basic principles of OCT.

System 100 includes an eye-visualization system 110, configured to provide a visual image of an imaged region in an eye 10, an Optical Coherence Tomographic (OCT) imaging system 120, configured to generate an OCT image of the imaged region; a refractometer 130, configured to generate a refractive mapping of the imaged region; and an analyzer 140, configured to determine refractive characteristics of the eye based on the OCT image and the refractive mapping. It will be appreciated that the OCT imaging system 120, the refractometer 130, and the analyzer/controller 140 can be integrated into the eye visualization system 110.

The imaged region can be a portion or a region of the eye 10, such as a target of a surgical procedure. In a corneal procedure, the imaged region can be a portion of a cornea 12. In a cataract surgery, the imaged region can be a capsule and the (crystalline) lens 14 of the eye. The imaged region may also include the anterior chamber of the eye, which includes both the cornea 12 and the lens 14. Alternatively, the imaged region may cover the full eye, including the cornea 12, the lens 14 and the retina 16. In a retinal procedure, the imaged region can be a region of the retina 16. Any combination of the above imaged regions can be an imaged region as well.

The eye-visualization system 110 can include a microscope 112. In some embodiments, it can include a slit-lamp. The microscope 112 can be an optical microscope, a surgical microscope, a video-microscope, or a combination thereof. In the embodiment of FIG. 1, the eye-visualization system 110 (shown in thick solid line) includes the surgical microscope 112, which in turn includes an objective 113, optics 115, and a binocular or ocular 117. The eye-visualization system 110 can also include a camera 118 of a video microscope.

System 100 further includes the Optical Coherence Tomographic (OCT) imaging system 120. The OCT imaging system 120 can generate an OCT image of the imaged region. The OCT imaging system can be configured to generate an A-scan or a B-scan of the imaged region. The OCT image or image information can be outputted in an "OCT out" signal that can be used by analyzer 140, for example, in combination with an outputted "Refractive out" signal to determine biometric or refractive characteristics of the eye.

OCT imaging system 120 can include an OCT laser operating at a wavelength range of 500-2,000 nm, in some embodiments at a range of 900-1,400 nm. The OCT imaging system 120 can be a time-domain, a frequency-domain, a spectral-domain, a swept-frequency, or a Fourier Domain OCT system 120.

In various embodiments, part of the OCT imaging system 120 can be integrated into the microscope, and part of it can be installed in a separate console. In some embodiments, the OCT portion integrated into the microscope can include only an OCT light source, such as the OCT laser. The OCT laser or imaging light, returned from the eye, can be fed into a fiber and driven to a second portion of the OCT imaging system 120, an OCT interferometer outside the microscope. The OCT interferometer can be located in a separate console, in some embodiments, where suitable electronics is also located to process the OCT interferometric signals.

Embodiments of the OCT laser can have a coherence length that is longer than an extent of an anterior chamber of the eye, such as the distance between a corneal apex to a lens apex. This distance is approximately 6 mm in most patients, thus such embodiments can have a coherence length in the 4-10 mm range. Other embodiments can have a coherence length to cover an entire axial length of the eye, such as 30-50 mm. Yet others can have an intermediate coherence length, such as in the 10-30 mm range, finally some embodiments can have a coherence length longer than 50 mm.

Some swept-frequency lasers are approaching these coherence length ranges. Some Fourier Domain Mode Locking (FDML) lasers, vertical-cavity surface-emitting laser (VCSEL)-based, polygon-based or MEMS-based swept lasers are already capable of delivering a laser beam with a coherence length in these ranges.

The example illustrated as system 100 further includes a refractometer 130 to generate a refractive mapping of the imaged region. The refractometer 130 may be any of the widely used types, including a laser ray tracer, a Shack-Hartmann, a Talbot-Moire, or another refractometer. The refractometer 130 can include a wavefront analyzer, an aberration detector, or an aberrometer. Some references use these terms essentially interchangeably or synonymously. A dynamic range of the refractometer 130 can cover both phakic and aphakic eyes, i.e., the eyes with and without the natural lens.

In some systems, the OCT imaging system 120 and the refractometer 130 can be integrated via a microscope interface 150 that can include a beam splitter 152c to provide an optical coupling into the main optical pathway of the microscope 112 or slit-lamp. A mirror 154-1 can couple the light of the refractometer 130 into the optical path, and a mirror 154-2 can couple the light of the OCT 120 into the optical path. The microscope interface 150, its beam splitter 152c, and mirrors 154-1/2 can integrate the OCT imaging system 120 and the refractometer 130 with the eye-visualization system 110.

In some embodiments, where the OCT imaging system 120 operates in the near infrared (IR) range of 900-1,400 nm, and the refractometer operates in the 700-900 nm range, the beam splitter 152c can be close to 100% transparent in the visible range of 400 nm-700 nm, and close to 100% reflective in the near-IR range of 700-1,400 nm range for high efficiency and low noise operations. By the same token, in a system where the mirror 154-1 redirects light into the refractometer 130, the mirror 154-1 can be close to 100% reflective in the near IR range of 700-900 nm, and the mirror 154-2 can be close to 100% refractive in the near IR range of 900-1,400 nm, redirecting to the OCT imaging system 120. Here, "close to 100%" can refer to a value in the 50-100% range in some embodiments, or to a value in the 80-100% range in others. In some embodiments, the beam splitter 152c can have a reflectance in the 50-100% range for a wavelength in the 700-1,400 nm range, and a reflectance in the 0-50% range for a wavelength in the 400-700 nm range.

FIG. 1 shows that the system 100 can include a second beam splitter 152b, in addition to the beam splitter 152c. The beam splitter 152c directs light between the objective 113 and the integrated OCT 120/refractometer 130 ensemble. The beam splitter 152b can direct light between a display 160 and the binocular 117. A third beam splitter 152a can direct light to the camera 118.

The analyzer, or controller, 140 can perform the integrated biometrical analysis based on the received OCT and refractive information. The analysis can make use of a wide variety of well-known optical software systems and products, including ray tracing software and computer-aided design (CAD) software. The result of the integrated biometry can be (1) a value of the optical power of portions of the eye and a corresponding suggested or prescribed diopter for a suitable IOL; (2) a value and an orientation of an astigmatism of the cornea, and suggested or prescribed toric parameters of a toric IOL to compensate this astigmatism;

and (3) a suggested or prescribed location and length of one or more relaxing incisions to correct this astigmatism, among others.

The analyzer 140 can output the result of this integrated biometry towards the display 160, so that the display 160 can display these results for the surgeon. Display 160 can be an electronic video-display or a computerized display, associated with the eye-visualization system 110. In other embodiments, the display 160 can be a display in close proximity of the microscope 112, such as attached to the outside of the microscope 112. Finally, in some embodiments, display 160 can be a micro-display, or heads-up display, that projects the display light into the optical pathway of the microscope 112. The projection can be coupled into the main optical pathway via a mirror 157. In other embodiments, the entire heads-up display 160 can be located inside the microscope 112, or integrated with a port of the microscope 112.

In previously available systems, the OCT engine and optics of microscope-mounted or microscope-integrated OCT systems, such as the one illustrated in FIG. 1, are non-configurable, with fixed system parameters, such as axial resolution, lateral resolution, and depth of focus. However, optimum system requirements for OCT differ, for different applications. For example, corneal and retinal applications typically require higher axial resolution than cataract-related procedures. Cataract applications, on the other hand, need a longer depth of focus for full-eye imaging or anterior-segment imaging, but typically obtain this longer depth of focus at the expense of compromised lateral resolution and axial resolution.

Various embodiments described herein provide microscope-based OCT apparatuses to flexibly address medical needs for cornea refractive, cataract, and vitreoretinal applications. As discussed in further detail below, the OCT engine and optics in various of these embodiments are reconfigurable, i.e., switchable, so that a single apparatus can provide optimum OCT performance for each of several operating modes or applications.

Figure 2:
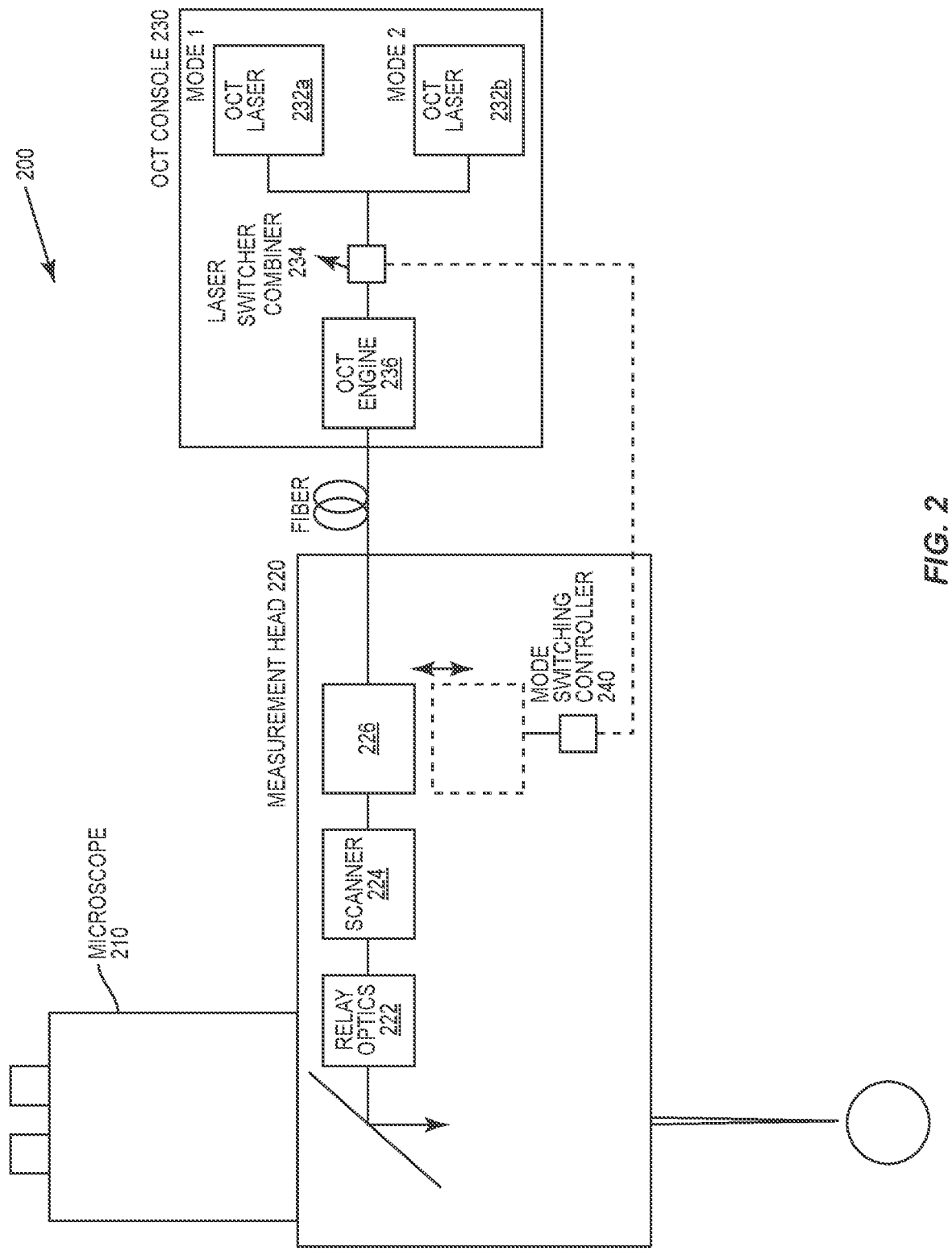
FIG. 2 illustrates an example OCT apparatus comprising selectable optical sources and a mode-switching optics unit.

FIG. 2 illustrates another embodiment of a system 200, in this case including mode-switching optics and laser-switching functionality consistent with some of the embodiments disclosed herein. While the basic functionality of system 200 is similar to that of system 100, as illustrated in FIG. 1, the components of system 200, as illustrated in FIG. 2, are grouped differently, for the purposes of discussion. It will be appreciated that the physical grouping may vary, from one embodiment to another.

System 200 includes a microscope unit 210, a measurement head 220, and an OCT console 230, as well as a mode switching controller 240. In some embodiments, measurement head 220 is mounted to a separate microscope unit 210, while in others the components of measurement head 220 are integrated into a single unit with microscope unit 210.

Microscope unit 210 may include some or all of the components shown in the eye-visualization system 110 of FIG. 1, including the microscope 112, which in turn includes an objective 113, microscope optics 115, up-beam and down-beam splitters 152u and 152d, and microscope binocular 117. Microscope unit 210 may further include a display 160, in some embodiments, and/or a camera 118, in some embodiments, as illustrated in FIG. 2. Because these details are not important to illustrate the operation of the mode-switching optics and laser-switching of the system 200 shown in FIG. 2, these details of microscope unit 210 are not shown in FIG. 2.

In the system 100 shown in FIG. 1, the OCT system 120 is illustrated as a single block. In FIG. 2, in contrast, the components of a configurable OCT imaging system are shown in more detail. In the example of FIG. 2, these components are divided between measurement head 220, which is integrated with or mounted on microscope unit 210, and OCT console 230. In some embodiments, some or all of the components shown in OCT console 230 may be included in a single unit with some or all of the components in measurement head 220, for example.

The OCT console 230 includes multiple light sources, in the illustrated example comprising OCT laser sources 232a and 232b. OCT console 230 further includes a laser switch/combiner 234, which allows for the selection of and/or combination of the outputs from laser sources 232a and 232b, in various embodiments. In some embodiments, laser switch/combiner 234 comprises an optical switch, permitting one or the other of outputs from laser sources 232a and 234b to be relayed to an OCT engine 236. In other embodiments, laser switch/combiner 234 may comprise an optical combiner, such that laser sources 232a and 232b are selected or combined by selectively powering or lasing on laser sources 232a and/or 232b. In still other embodiments, laser switch/combiner 234 may combine both an optical switch and an optical combiner. It should be noted that while only two laser sources are shown in the example system 200 of FIG. 2, other systems might include three or more distinct laser sources, with each having different optical characteristics that are useful for different OCT applications. Alternatively, a system might have a single laser source, but with switchable operational modes for the laser source. The switching between different sources and/or operational modes may allow the switching between an optical source suitable for long-range and low-resolution imaging and a source suitable for short-range and high-resolution imaging.

OCT engine 236 includes an interferometer, beam splitting, reference beam length adjustment, as well as an OCT detector and digitizer. OCT engine 236 may further comprise a camera and frame grabber, in some embodiments. The details of interferometry for OCT are well known and not provided here, but it will be understood that OCT engine 236 may be configured for time-domain OCT, in which case it includes functionality for scanning the reference arm, or for spectral-domain OCT, or for swept-source OCT. In embodiments as disclosed herein, the interferometer may be configured so that it supports the use of any of several laser sources, e.g., so that the components of the interferometer are configured to handle any of several different laser wavelengths, for example.

Measurement head 220 includes relay optics 222, scanner 224, and mode-switching optics 226. Scanner 224 comprises the circuitry and mechanics for performing x-y scanning across the imaged object (z-axis scanning is performed by OCT engine 236), while relay optics 222 include any optical components necessary for beam deliver from the scanner to the imaged object (e.g., an imaged cornea), and more generally to couple the forward and reflected beams between the scanner and the imaged object. These may include, for example, an additional beam expander/reducer, a focusing lens, and/or lens combinations. Mode-switching optics 226 include one or several optical stages, where the optical components for one or more of these optical stages can be swapped out or adjusted, according to two or different operating modes, under the control of mode-switching controller 240. In other words, the mode-switching optics can change/adjust the optical performance of the beam delivery path, based on the selection of one of several possible operating modes.

Figure 6A:
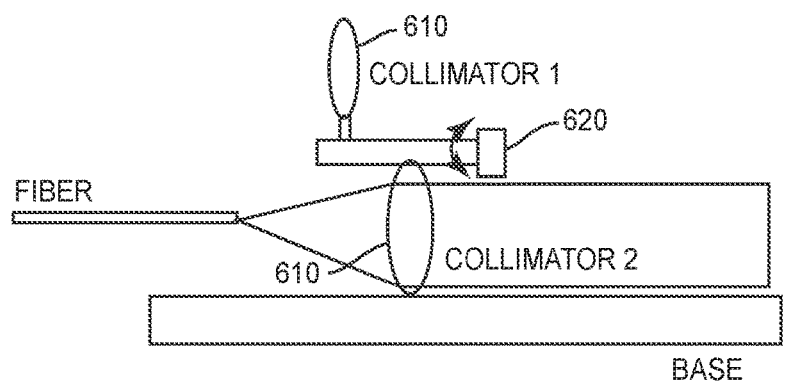
FIG. 6A illustrates components that might be found in an example mode-switching optics module.
Figure 6B:
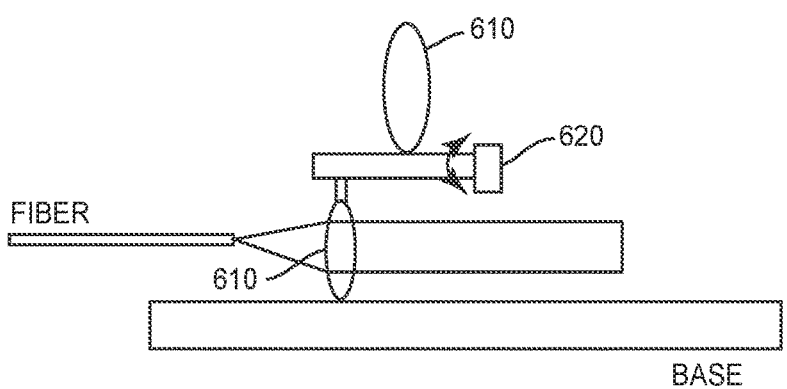
FIG. 6B illustrates components that might be found in an example mode-switching optics module.
Figure 6C:
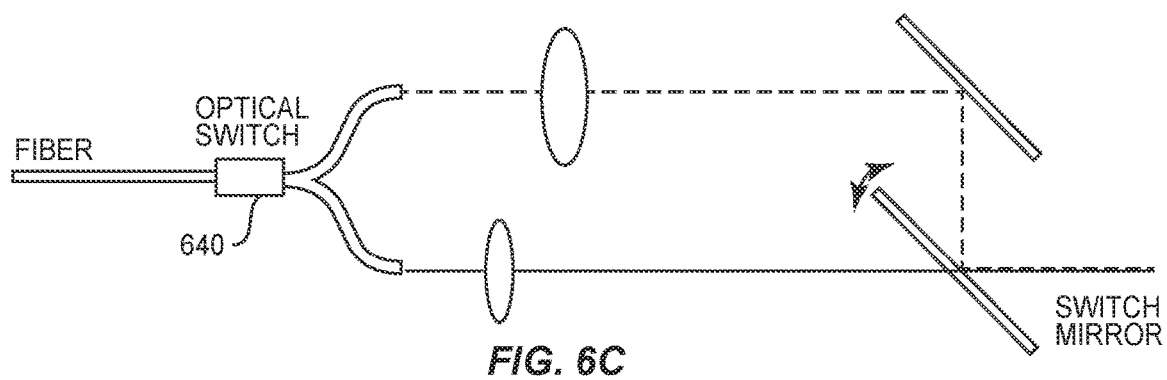
FIG. 6C illustrates components that might be found in an example mode-switching optics module.
Figure 6D:
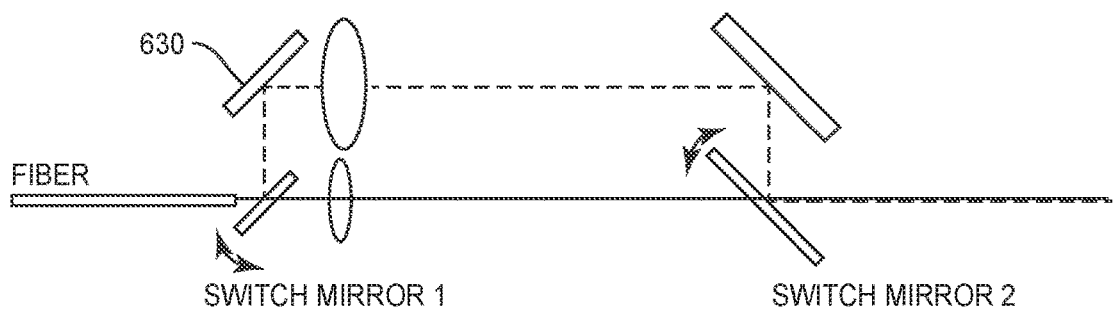
FIG. 6D illustrates components that might be found in an example mode-switching optics module.

FIG. 6A-6D shows several examples of switchable or configurable optics that might be included in mode-switching optics 226. For example, mode-switching optics 226 may be configured so that a beam expander or beam reducer can be selected, e.g., moved in or out of an optical path, to change beam parameters for first and second operating modes. Mode-switching optics 226 may comprise two different collimators 610 with different focal lengths, for example, configured to provide different beam diameters to the input of the scanner, where mode-switching controller 240 selects one of the collimators according to a desired operating mode. This switching between two different collimators 610 is shown in FIGS. 6A and 6B, for example, where the switching is performed with a motor 620. In some embodiments, a switchable mirror 630 (or galvanometer mirror, MEMS mirror) can be used to change the beam direction to go through different optics; in still other embodiments, an optical fiber switch 640 can be used to switch between different optical paths and optics. These alternatives are shown in FIGS. 6C and 6D. More generally, the selectable/adjustable optics in mode-switching optics 226 may provide for different lateral resolutions and depths of focus, for example, according to two or more different operating modes.

Referring back to FIG. 2, mode-switching controller 240 comprises circuitry for taking as input a selection of an operating mode (e.g., from a user interface, not shown) and providing the control signals for selecting the configurable optics in mode-switching optics 226 and the selectable laser sources and/or source operating modes in OCT console 230, e.g., via laser switcher/combiner 234. Mode-switching controller 240 may comprise a processor circuit coupled with program memory, or digital logic, or a combination of both, and may be configured, for example, to determine a set of control signals for application to mode-switching optics 226 and OCT console 230, based on a selected operating mode, e.g., using a look-up table or other mapping of operational mode to optics settings or control signals.

Figure 3:
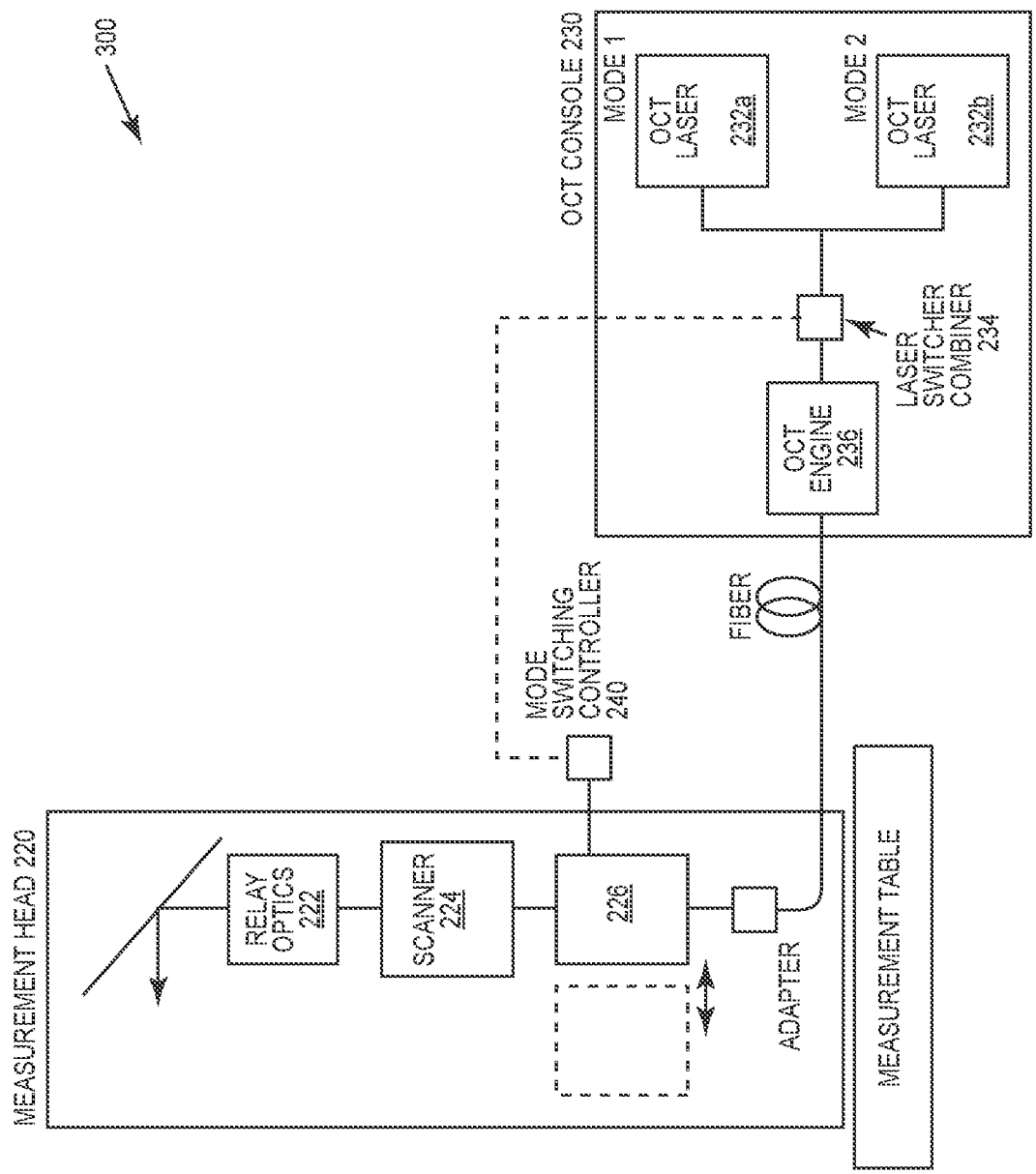
FIG. 3 illustrates another example OCT apparatus comprising selectable optical sources and a mode-switching optics unit.

In the example embodiment shown in FIG. 2, the measurement head 220 is attached to a surgical microscope unit 210, for instrasurgical applications. FIG. 3 illustrates an embodiment of an OCT apparatus 300 in which the measurement head 220 is mounted on a measurement table, for clinic applications. The functionality of the various components shown in FIG. 3 may be identical or similar to that of the components shown in FIG. 2, in some embodiments, but the optical components may vary, depending on the particular applications or range of applications for which the equipment is intended.

Figure 4:
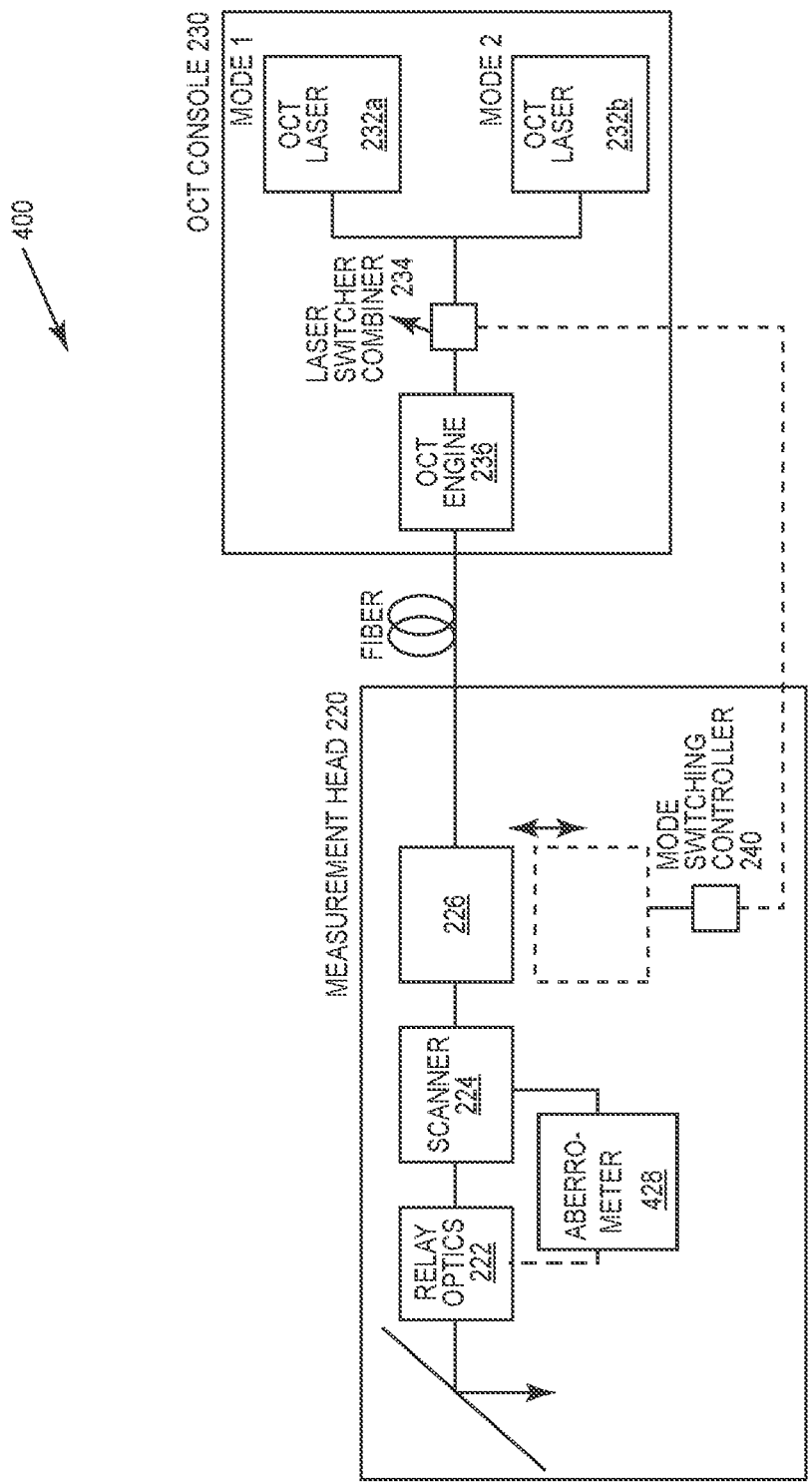
FIG. 4 illustrates another example OCT apparatus comprising selectable optical sources and a mode-switching optics unit.

Similarly, FIG. 4 shows an embodiment of an OCT apparatus 400, in which a measurement head 320 combines both OCT functionality as well as an aberrometer 428. The aberrometer 428 could be based on ray-tracing, for example, in which case it may share the scanning functionality with the OCT functions. Alternatively, aberrometer 428 may be based on Schack Hartman or Talbot Moire technologies, for example, in which case it may be coupled into the optical path through a dichroic beam splitter.

With the above detailed examples in mind, it will be appreciated that an example optical coherence tomography (OCT) apparatus embodying one or more of the devices and techniques describe herein includes an optical source module comprising two or more selectable optical sources or an optical source configured to selectively operate in two or more source operating modes, or a combination of both, and further comprises an OCT engine coupled to the optical source module, the OCT engine comprising an OCT interferometer. This example OCT apparatus still further includes a mode-switching optics module coupled to the OCT engine and comprising one or more swappable, selectable, or adjustable optical components, such that the mode-switching optics module is configured to selectively provide two or more optical configurations for the optical path between the OCT engine and an imaged object, according to two or more corresponding operating modes. It should be appreciated that the term "module" is used herein to refer to an assembly of devices, such as optical devices, electronic devices, where the module may also comprise circuit boards, mounting apparatuses, housings, connectors, and the like.

In some embodiments, the OCT apparatus further includes a mode-switching controller configured to (a) control the optical source module to select an optical source and/or source operating mode, and (b) control the mode-switching optics module to select one of the two or more optical configurations for the optical path, based on a selected operating mode. In some embodiments, the mode-switching controller is configured to receive, from a user interface, an indication of the selected operating mode. In some embodiments, the OCT apparatus further comprises a microscope coupled to the mode-switching optics and configured for viewing an imaged object scanned by the OCT apparatus.

In some embodiments, the optical source module comprises an optical switch configured to switch an output of a selected one of the two or more selectable optical sources, for relaying to the OCT engine. In some of these and in some other embodiments, the optical source module comprises an optical combiner configured to combine outputs from the two or more selectable optical sources, where the two or more selectable optical sources are configured to be selected by selectively powering or lasing on one of the selectable optical sources.

In some embodiments, the mode-switching optics module comprises a beam expander element or beam reducer element, where the beam expander element or beam reducer element is configured to be selectively moved in or out of the optical path, to change beam parameters for at least first and second operating modes. In some of these and in some other embodiments, the mode-switching optics module comprises first and second collimators, having different focal lengths, where the first and second selectable collimators are configured to be selectable according to a desired operating mode. In some of these latter embodiments, the mode-switching optics module comprises a switchable mirror controllable to selectively change an optical beam direction to pass through the first collimator or second collimator, depending on a selected operating mode, while in others the mode-switching optics module comprises an optical fiber switch controllable to selectively direct an optical beam through the first collimator or second collimator, depending on a selected operating mode.

Figure 5:
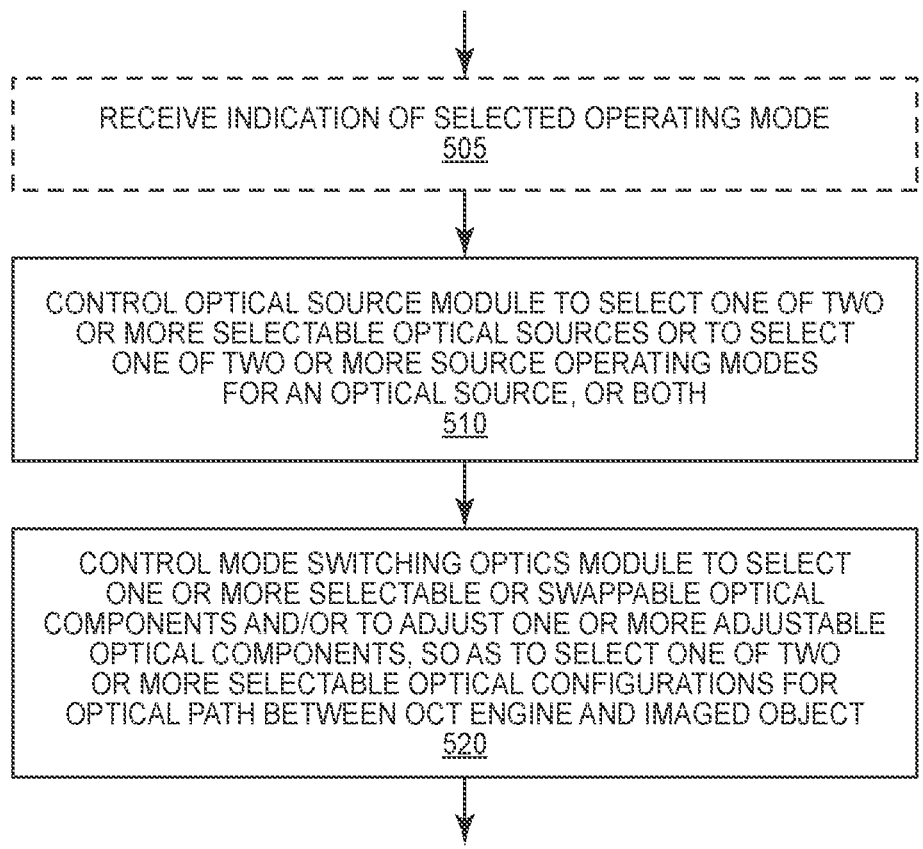
FIG. 5 is a process flow diagram illustrating an example method according to techniques disclosed herein.

FIG. 5 illustrates an example method suitable for implementation in an OCT apparatus, such as an OCT apparatus configured according to any of the above examples. As seen at block 510, the method comprises controlling an optical source module to select one of two or more selectable optical sources or to select one of two or more source operating modes for an optical source, or a combination of both. As seen at block 520, the method further comprises controlling a mode-switching optics module coupled to the optical source module via an OCT engine, the OCT engine comprising an interferometer, to select one or more swappable optical components or to adjust one or more adjustable optical components, so as to select one of two or more selectable optical configurations for the optical path between the OCT engine and an imaged object.

In some embodiments, the method further comprises receiving, from a user interface, an indication of the selected operating mode, wherein said controlling of the optical source module and the mode-switching optics module is responsive to the received indication. This is shown at block 505, which is illustrated with a dashed outline to indicate that it need not be present in every embodiment or instance of the illustrate method.

In some embodiments, controlling the optical source module comprises controlling an optical switch configured to switch an output of a selected one of the two or more selectable optical sources, for relaying to the OCT engine. In other embodiments, controlling the optical source module comprises selectively powering or lasing on one of the two or more selectable optical sources.

In some embodiments, controlling the mode-switching optics module comprises controlling the mode-switching optics to move a beam expander or beam reducer in or out of the optical path, to change beam parameters for at least first and second operating modes. In some of these and in some other embodiments, controlling the mode-switching optics module comprises selecting between at least first and second collimators, having different focal lengths, where the first and second selectable collimators are configured to be selectable according to a desired operating mode. In some of these latter embodiments, controlling the mode-switching optics module comprises controlling a switchable mirror to selectively change an optical beam direction to pass through the first collimator or second collimator, depending on a selected operating mode, while in others, an optical fiber switch is controlled to selectively direct an optical beam through the first collimator or second collimator, depending on a selected operating mode.

The specific embodiments described above illustrate but do not limit the invention. It should also be understood that numerous modifications and variations are possible in accordance with the principles of the present invention, as described above and as claimed below.

What is claimed is:

1. An optical coherence tomography (OCT) apparatus, comprising:
   an optical source module comprising two or more selectable optical sources;
   a single OCT engine coupled to the optical source module, the OCT engine comprising an OCT interferometer; and
   a mode-switching optics module coupled to the OCT engine and comprising one or more swappable, selectable, or adjustable optical components, such that the mode-switching optics module is configured to selectively provide two or more optical configurations for the optical path between the OCT engine and an imaged object, according to two or more corresponding operating modes, the mode-switching optics selecting between the two or more selectable optical sources.

2. The OCT apparatus of claim 1, further comprising a mode-switching controller configured to (a) control the optical source module to select an optical source, and (b) control the mode-switching optics module to select one of the two or more optical configurations for the optical path, based on a selected operating mode.

3. The OCT apparatus of claim 2, wherein the mode-switching controller is configured to receive, from a user interface, an indication of the selected operating mode.

4. The OCT apparatus of claim 1, wherein the optical source module comprises an optical switch configured to switch an output of a selected one of the two or more selectable optical sources, for relaying to the OCT engine.

5. The OCT apparatus of claim 1, wherein the optical source module comprises an optical combiner configured to combine outputs from the two or more selectable optical sources, and wherein the two or more selectable optical sources are configured to be selected by selectively powering or lasing on one of the selectable optical sources.

6. The OCT apparatus of claim 1, wherein the mode-switching optics module comprises a beam expander element or beam reducer element, wherein the beam expander element or beam reducer element is configured to be selectively moved in or out of the optical path, to change beam parameters for at least first and second operating modes.

7. The OCT apparatus of claim 1, wherein the mode-switching optics module comprises first and second collimators, having different focal lengths, wherein the first and second selectable collimators are configured to be selectable according to a desired operating mode.

8. The OCT apparatus of claim 7, wherein the mode-switching optics module comprises a switchable mirror controllable to selectively change an optical beam direction to pass through the first collimator or second collimator, depending on a selected operating mode.

9. The OCT apparatus of claim 7, wherein the mode-switching optics module comprises an optical fiber switch controllable to selectively direct an optical beam through the first collimator or second collimator, depending on a selected operating mode.

10. The OCT apparatus of claim 1, further comprising a microscope coupled to the mode-switching optics and configured for viewing an imaged object scanned by the OCT apparatus.

11. A method, in an optical coherence tomography (OCT) apparatus, the method comprising:
    controlling an optical source module comprising one of two or more selectable optical sources; and
    controlling a mode-switching optics module coupled to the optical source module via a single OCT engine, the single OCT engine comprising an interferometer, to select one or more selectable or swappable optical components and/or to adjust one or more adjustable optical components, so as to select one of two or more selectable optical configurations for the optical path between the single OCT engine and an imaged object, the mode-switching optics selecting between the two or more selectable optical sources.

12. The method of claim 11, further comprising receiving, from a user interface, an indication of the selected operating mode, wherein said controlling of the optical source module and the mode-switching optics module is responsive to the received indication.

13. The method of claim 11, wherein controlling the optical source module comprises controlling an optical switch configured to switch an output of a selected one of the two or more selectable optical sources, for relaying to the OCT engine.

14. The method of claim 11, wherein controlling the optical source module comprises selectively powering or lasing on one of the two or more selectable optical sources.

15. The method of claim 11, wherein controlling the mode-switching optics module comprises controlling the mode-switching optics to move a beam expander or beam reducer in or out of the optical path, to change beam parameters for at least first and second operating modes.

16. The method of claim 11, wherein controlling the mode-switching optics module comprises selecting between at least first and second collimators, having different focal lengths, wherein the first and second selectable collimators are configured to be selectable according to a desired operating mode.

17. The method of claim 16, wherein controlling the mode-switching optics module comprises controlling a switchable mirror to selectively change an optical beam direction to pass through the first collimator or second collimator, depending on a selected operating mode.

18. The method of claim 16, wherein controlling the mode-switching optics module comprises controlling an optical fiber switch to selectively direct an optical beam through the first collimator or second collimator, depending on a selected operating mode.

* * * * *